(12) United States Patent
Nimal

(10) Patent No.: US 9,889,012 B2
(45) Date of Patent: Feb. 13, 2018

(54) BIOMEDICAL DEVICE, METHOD FOR MANUFACTURING THE SAME AND USE THEREOF

(71) Applicant: Didier Nimal, Gif-sur-Yvette (FR)

(72) Inventor: Didier Nimal, Gif-sur-Yvette (FR)

( * ) Notice: Subject to any disclaimer, the term of this patent is extended or adjusted under 35 U.S.C. 154(b) by 657 days.

(21) Appl. No.: 14/487,464

(22) Filed: Sep. 16, 2014

(65) Prior Publication Data

US 2015/0004042 A1 Jan. 1, 2015

Related U.S. Application Data

(63) Continuation-in-part of application No. 13/355,845, filed on Jan. 23, 2012, now Pat. No. 8,862,258, which
(Continued)

(30) Foreign Application Priority Data

Jul. 23, 2009 (WO) .................. PCT/IB2009/054225

(51) Int. Cl.
*B22F 3/105* (2006.01)
*A61F 2/28* (2006.01)
(Continued)

(52) U.S. Cl.
CPC ................ *A61F 2/28* (2013.01); *A61L 27/12* (2013.01); *A61L 27/56* (2013.01); *B05D 1/02* (2013.01);
(Continued)

(58) Field of Classification Search
None
See application file for complete search history.

(56) References Cited

U.S. PATENT DOCUMENTS 4,863,538 A 9/1989 Deckard
6,454,811 B1 9/2002 Sherwood et al.
(Continued)

FOREIGN PATENT DOCUMENTS

WO 2009/053835 4/2009

OTHER PUBLICATIONS

Tampieri et al. "Porosity-graded hydroxyapatite ceramics to replace natural bone" Biomaterials, vol. 22, No. 11, Jun. 2001, pp. 1365-1370.
(Continued)

*Primary Examiner* — Jessee Roe
*Assistant Examiner* — Ngoclan T Mai
(74) *Attorney, Agent, or Firm* — Young & Thompson

(57) ABSTRACT

A method for manufacturing a three-dimensional biomedical device for fitting in a bone defect having an osteoinductive first area with a controlled porosity and a second area, which is produced by laser technology from an absorbent and from a first powder including one of ceramics, metals, metal alloys, bioactive glasses, lead zirconate titanate and biocompatible polymers, or mixtures thereof, wherein the ratio of the porosities from the second area to the first area is equal or less than one, preferably from 0.001 to 0.9, wherein a virtual object is designed with a computer-aid designed software, and the device is manufactured by laser technology including layering a powder onto a plate (7) so that a layer of a predetermined thickness is formed; the laser beam (8) selectively processes the powder to produce a processed layer, and, thus, layer after layer, the layers are joined together until the biomedical device is formed.

14 Claims, 5 Drawing Sheets

Related U.S. Application Data is a continuation-in-part of application No. PCT/EP2010/058941, filed on Jun. 23, 2010, now abandoned.

(51) Int. Cl.
| | |
|---|---|
| *A61L 27/56* | (2006.01) |
| *A61L 27/12* | (2006.01) |
| *B28B 1/00* | (2006.01) |
| *B05D 1/02* | (2006.01) |
| *C04B 35/119* | (2006.01) |
| *C23C 16/44* | (2006.01) |
| *B22F 3/11* | (2006.01) |
| *B29C 67/00* | (2017.01) |
| *B29K 101/12* | (2006.01) |

(52) U.S. Cl.
CPC .............. *B22F 3/1055* (2013.01); *B22F 3/11* (2013.01); *B28B 1/001* (2013.01); *C04B 35/119* (2013.01); *C23C 16/4417* (2013.01); *A61L 2430/02* (2013.01); *B22F 2998/10* (2013.01); *B29C 67/0077* (2013.01); *B29K 2101/12* (2013.01); *Y02P 10/295* (2015.11)

(56) References Cited

U.S. PATENT DOCUMENTS

| | | |
|---|---|---|
| 6,993,406 B1 | 1/2006 | Cesarano, III |
| 8,048,150 B2 | 11/2011 | Weber et al. |
| 2003/0074096 A1 | 4/2003 | Das et al. |
| 2003/0114936 A1 | 6/2003 | Sherwood et al. |
| 2003/0175410 A1 | 9/2003 | Campbell et al. |
| 2004/0243237 A1 | 12/2004 | Unwin |
| 2005/0177238 A1 | 8/2005 | Khandkar |
| 2006/0052875 A1 | 3/2006 | Bernero et al. |
| 2006/0147332 A1* | 7/2006 | Jones ............... A61F 2/2803 419/8 |
| 2006/0198939 A1 | 9/2006 | Smith et al. |
| 2007/0003753 A1 | 1/2007 | Asgari |
| 2007/0118243 A1 | 5/2007 | Schroeder et al. |
| 2007/0183918 A1 | 8/2007 | Monsheimer et al. |
| 2007/0210493 A1 | 9/2007 | Takahashi et al. |

OTHER PUBLICATIONS

International Search Report dated Feb. 4, 2011, corresponding to International Application No. PCT/EP2010/058941.

* cited by examiner

BIOMEDICAL DEVICE, METHOD FOR MANUFACTURING THE SAME AND USE THEREOF

This application is a continuation-in-part of U.S. application Ser. No. 13/355,845, filed Jan. 23, 2012, now U.S. Pat. No. 8,862,258.

FIELD OF INVENTION

This invention relates to the field of the manufacture of implants for medical and/or orthopedic applications, such as for example prostheses, orthodontia, bone implants, preferably cranial implants. More precisely, the present invention relates to a method of manufacturing a biomedical device from ceramic or metal powder, using a laser technology.

BACKGROUND OF INVENTION

The growing search for new materials for orthopedic or reconstruction surgery, leads to the development, in the last two decades, of biomedical devices based on ceramics, such as hydroxyapatite and tricalcium phosphate. These ceramic materials were recognized as biocompatible and as having an osseoconductive behavior, and were thus used for the repair or replacement of bone defects.

Aiming a controlled porosity of these materials while keeping satisfactory mechanical properties, remains the technical challenge of these biomaterials. Efforts in manufacturing porous ceramics with interconnected pores have been made in order to enhance tissue growth. It is known that a porous and interconnected structure allows new tissue to penetrate the substrate, and stimulates the growth of new bone tissue.

For example, WO 2009/053835, as well as a number of the prior art documents in the field, reports a method to make biomedical devices with controlled porosity, involving the replication in ceramics of 3D-substrates such as polymeric substrates, which are eliminated at the end of the process by sintering. This method has the disadvantage of necessitating several steps, first for the manufacture of the substrate and second for the elimination/release of the substrate. Furthermore, the release of the substrate is susceptible to result in cracking phenomena on the thin walls of the piece. To avoid these drawbacks, additives are used. Most of the time, these additives are not biocompatible. Moreover, there is a remaining high risk that the step of elimination of the substrate may cause a distortion in the work piece due to variations of the dimensions during the warm-up. For these reasons, elimination of the substrate may be a hazardous step that the present invention intends to avoid.

The present invention is thus advantageous, in that the process of the invention involves direct laser treatment of the powder without use of a substrate, which is time effective, avoids the risk of distortion of the work piece, and is free of additives. Consequently, the product resulting from the manufacturing process of the invention is also free of additives.

Some prior art documents related to ceramic devices avoid the use of polymeric substrates and directly mix powders, such as for example, U.S. patent application 2007/0210493. This U.S. patent application reports the manufacture of porous ceramics based on slurry prepared by mixing alumina particles, glass frit, silica particles, silica sol and water. This mixture is set in a plate, dried and sintered in order to obtain a hard and resistant ceramic. However, this method leads to a filter for filtering fluid such as liquid and gas or the like, and is not adapted for a biomedical device.

Further prior art relates to methods of manufacturing three-dimensional objects by laser technology. U.S. Pat. No. 4,863,538 for example, reports how to make a three-dimensional objet from a powder of plastic, metal, polymer, ceramic powders, or composite materials. The reported method is a layer-wise method: the powder is dispensed into a target area where the laser selectively sinters the powder to produce a sintered layer; the layers are joined together until the completed part is formed.

Technical Issue

There is thus still a need for simple methods for manufacturing biocompatible implants, avoiding multi-step processing. There is also a high expectation in this industry for safer and cost effective methods for manufacturing biocompatible implants avoiding the use of molds, which may lead to the need of further machining steps and/or to the use of substrate or binding agent. There is also a need for methods not involving the use of additives.

The present invention avoids the drawbacks of the prior art methods, as it is a one-step method for a direct manufacturing of a tridimensional object from a three-dimensional virtual object through laser technology, without using any mold.

The method of the invention is very advantageous in that it makes it easy to shape an implant perfectly matching the shape of the defect site and it does not involve the manufacturing of a specific mold for each defect. A close fit between the implant and defect site is desirable because (1) it can improve the healing of the defect after implantation, by for example facilitating the influx of cells, and (2) it ensures that the implant remains in the desired position within the defect. This invention is not limited in any way regarding the shape of the work piece, and makes it easy to manufacture complex, unique, customized work pieces, with an industrial scale. The method of the invention is also advantageous as it may utilize any kind of material suitable with laser technology, for the manufacture of the implant.

Another advantage of the method of the invention is to result, if desired, in a biocompatible material having a controlled porosity.

SUMMARY

The present invention relates to a method for manufacturing a biomedical device for fitting bone defect, said biomedical device having at least one osteoconductive first area with a controlled porosity and at least one porous second area, the ratio of the porosity of the second area to the porosity of the first area being equal or less than one, wherein the device is produced by a laser technology from an absorbent and from a first powder comprising a material selected from the group consisting of ceramics, metals, metal alloys, bioactive glasses, lead zirconate titanate, biocompatible polymers, and mixtures thereof, wherein the laser is a pulsed laser or a continuous laser of 100 to 1200 watts, and the laser progression speed of the laser beam ranges from 0.01 and 5000 mm/s; and wherein
- an image of the defect is performed,
- from this image, a virtual object is designed with a computer-aid designed software,
- optionally, a scale model is performed,
- the biomedical device is manufactured by a laser technology comprising:

layering onto a plate either:
a mixture of the first powder and the absorbent;
the first powder coated with the absorbent; or
the first powder, whereon subsequently the absorbent is selectively deposited in a predefined trajectory;
so that a layer of a predetermined thickness is formed on the plate,
having the laser beam selectively processed the layer to produce a processed layer, and this, layer after layer, the layers being joined together until the completed biomedical device is formed.

According to one embodiment, the absorbent comprises carbon, scandium, titanium, vanadium, chromium, manganese, iron, cobalt, nickel, copper, or zinc or any compound comprising at least one of said chemical elements, or mixture thereof.

According to one embodiment, the absorbent is selectively deposited by means of a nozzle, a spray, a jet or a printing head.

According to one embodiment, the first powder is coated with the absorbent by chemical vapor deposition or any process enabling the coating of a powder, e.g. wet process.

According to one embodiment, particles of the first powder have a granulometry of 1 to 500 micrometers.

According to one embodiment, the particle size of the absorbent ranges from 1 nanometer to 500 micrometers, preferably from 1 nanometer to 200 micrometers, more preferably from 10 nanometers to 100 nanometers.

According to one embodiment, the thickness of the layer of powder ranges from 0.1 to 2000 micrometers.

According to one embodiment, a step of heating the powder is achieved prior to the layering step, at a temperature of 200 to 1500° C.

According to one embodiment, a step of thermic post-treatment is achieved at a temperature of 200-1200° C. for removing the absorbent.

According to one embodiment, the laser is a 160 watts laser.

According to one embodiment, the laser is adjusted at 1 to 25% of the total power of the laser.

Definitions

In the present invention, the following terms have the following meanings:

The term "absorbent" refers to an inorganic additive intended to absorb a proportion of laser energy (i.e. a given range of laser wavelengths) and to dissipate it in another form of energy such as calorific energy. Additive means that the three-dimensional biomedical device substantially does not comprise the absorbent at the end of the manufacturing process, preferably contains less than 0.5% of absorbent. Added to a non-absorbent or poorly absorbent material, the absorbent enhances the laser sintering process by dissipating energy (e.g. calorific energy) to the surrounding material. The absorbent comprises a specific absorptivity higher than the specific absorptivity of the first powder.

The term "first area" as used herein means an area of the implant that is proximal and/or in contact, when in situ, with the borders or limits of the defect, and susceptible to be colonized in situ by the patient cells, such as for example the patient osteoblasts. According to an embodiment, all or part of the first area is colonizable by osteoblasts, and when colonized, has mechanical properties very close to the mechanical properties of the adjacent bone. Advantageously, the first area is colonized at its edge, which is very close or in contact with the natural tissue when implanted. According to the invention, the osteoconductive porous first area is colonizable in situ with osteoblasts and behaves as a support for growth of osteoblasts. As used herein, the first area is the outer or peripheral area of the implant, i.e. the area which is, in situ, in contact or proximal with tissue for example bone tissue. Said first area isolates, when in situ, a second area from tissue in contact with the first area. Proximal means that the first area is located, when in situ, within a distance which enables cell migration and then osteoconduction, preferably a distance ranging from 0.1 micrometer to 1 centimeter. According to one embodiment, the first area is, in its thickness, in contact or proximal, when in situ, with the surrounding tissue.

The term "second area" as used herein means an area which may not be colonized in situ by the patient cells, because it distant i.e. spatially isolated from the borders or limits of the defect by means of the first area and/or because it is made of non-colonizable material for example with a low osteoconductivity or osteoinductivity material, or because its low porosity does not make it possible for the cells to colonize. In an embodiment, the second area is tight. As used herein, the second area is located at the inner part of the implant, i.e. the surface or the volume which is, in situ, isolated from tissue in contact with the first area or isolated from the exterior environment.

The term "biomaterial" as used herein means a material that is biocompatible with a human or animal body. The biomaterial may be comprised within, or may be, an implant or tissue scaffold and does not include the absorbent used in the manufacturing process.

The term "implantable" as used herein means capable to be surgically grafted, inserted or embedded in an animal, including human, body.

The term "layer" refers, except if otherwise specified, to the layer deposited onto the plate which can be either a powder of the first powder mixed with an absorbent or a first powder with an absorbent selectively deposited thereon. This layer is then processed by a laser beam.

The term "particle" as used herein means a fragment or small piece of material.

The term "porous" as used herein refers to a substrate that comprises pores holes or voids, rendering the biomaterial osteoconductive. Osteoconductivity typically refers to features associated with pores having a diameter equal or greater than approximately 10 micrometers, preferably from 10 to 1000 micrometers, more preferably from 100 to 800 micrometers, still more preferably from 200 to 600 micrometers, even more preferably 300 to 500 micrometers.

The term "porosity" refers to a measure of the void spaces in the biomaterial of the invention, and is measured as a fraction, between 0-1, or as a percentage between 0-100%. According to the present invention, porosity is measured with SEM, i.e. Scanning Electro Microscopy (microscope JSM 6300 of the JEOL company, tension 15 KV): samples of "first area" are invested in a polymethylmethacrylate resin, and then polished and made conductor by the depot a thin layer of Gold-Palladium; 8 images (×20 scale) are acquired for each sample. Porosity is then assessed by an image analysis software using a technique of grey thresholding. The same method is applied to assess the porosity of the <<second area>>.

The term "controlled porosity" refers to the porosity programmed through the virtual object prior to the launching of the manufacture process. Pore parameters such as pore sizes (width, length or diameter, shape), pore orientations, pore distributions or interconnections are programmed (i.e. defined and modelized) before the manufacturing process by means of a 3D computer-aid design software for example. The laser sintering process for realizing three-dimensional article comprises a computer file storing a description layer by layer of the three-dimensional structure to manufacture, especially programmed parameters related to porosity. Thus the 3D biomedical device modelisation with said controlled porosity is reproduced according to imposed programmed parameters. On the contrary, non-controlled porosity resulting from the manufacturing process and parameters is not voluntary and may be considered as an artifact of the process.

The term "powder" refers to a material composed of very fine particles that are not cemented together. In the present invention, powder refers either to the first powder or to a mixture of the first powder and an absorbent in the form of a powder.

The term "first powder" refers to a powder comprising a material selected from the group consisting of ceramics, metals, metal alloys, bioactive glasses, lead zirconate titanate, biocompatible polymers, and mixtures thereof. The three-dimensional biomedical device is entirely made of the first powder at the end of the manufacturing process.

The term "non-resorbable" as used herein means substantially not susceptible to be absorbed or eliminated by an animal body, including human body, through a physiological process.

The term "selectively" refers to the fact that the absorbent, if deposited onto a layer of first powder (i.e. not mixed with the first powder; or coated on the first powder prior to the manufacturing process) is deposited on selected location, depending of the pre-defined trajectory of the laser. The absorbent is indeed deposited in a controlled way on/near the pre-defined trajectory of the laser beam.

The term "laser progression speed" refers to the velocity of the laser focus beam across the layer to be sintered and therefore determines the speed of the manufacturing process.

The term "synthetic" as used herein means artificially produced.

The term "substantially not degradable" means less than 10% of resorbability by year.

DETAILED DESCRIPTION

This invention thus relates to a three-dimensional biomedical device, having an osteoconductive first area with a controlled porosity and a second area, the device being produced by a laser technology from a powder comprising ceramics; and/or metals; and/or metal alloys; and/or bioactive glasses; and/or lead zirconate titanate; and/or biocompatible polymers and/or mixtures thereof.

This invention also relates to a three-dimensional biomedical device, having an osteoconductive first area with a controlled porosity and a second area, the device being produced by a laser technology from an absorbent and a first powder comprising ceramics; and/or metals; and/or metal alloys; and/or bioactive glasses; and/or lead zirconate titanate; and/or biocompatible polymers and/or mixtures thereof.

This invention further relates to a method for manufacturing a biomedical device for fitting bone defect, said biomedical device having at least one osteoconductive first area with a controlled porosity and at least one porous second area, the ratio of the porosity of the second area to the porosity of the first area being equal or less than one, wherein the device is produced by a laser technology from an absorbent and from a first powder comprising a material selected from the group consisting of ceramics, metals, metal alloys, bioactive glasses, lead zirconate titanate, biocompatible polymers, and mixtures thereof, wherein the laser is a pulsed laser or a continuous laser of 100 to 1200 watts, and the laser progression speed of the laser beam is ranging from 0.01 and 5000 mm/s; and wherein an image of the defect is performed,
from this image, a virtual object is designed with a computer-aid designed software,
optionally, a scale model is performed,
the biomedical device is manufactured by a laser technology comprising:
  layering onto a plate either:
    a mixture of the first powder and the absorbent in the form of a powder;
    the first powder coated with the absorbent; or
    the first powder, whereon subsequently a layer of the absorbent is selectively deposited in a predefined trajectory;
  so that a layer of a predetermined thickness is formed on the plate,
  having the laser beam selectively processed the layer to produce a processed layer, and this, layer after layer, the layers being joined together until the completed biomedical device is formed.

According to one embodiment, the mixture of the first powder and the absorbent in the form of a powder is achieved before the manufacturing process. According to one embodiment, the coating of the first powder with the absorbent is achieved prior to the manufacturing process.

Ceramics may be preferably selected from alumina or alumina derivative such as for example aluminosilicate; ceramic phosphates preferably tricalcium phosphate; apatite derivatives, preferably hydroxyapatite (including synthetic hydroxyapatite, more preferably substantially not degradable synthetic hydroxyapatite, carbonate-substituted hydroxyapatite, silicate-substituted hydroxyapatite); fluoroapatite or fluorohydroxyapatite or silicated apatite; zirconia, zirconia derivatives, zirconia-toughened alumina (ZTA), alumina-toughened-zirconia (ATZ), alumina-zirconia, ytria-zirconia (TZP), wallostonite.

Metals and/or metal alloys are preferably selected from titanium; titanium alloys such as for example titanium-aluminum-vanadium; chrome-cobalt and alloys thereof, titane-nickel alloys such as for example nitinol, stainless steel.

Bioactive glasses are recognized as materials suitable for bone repair or replacement. Bioglasses preferred in the present invention are silicate type materials composed of $SiO_2$, $CaO$ and optionally $Na_2O$, and/or $P_2O_5$. Preferred bioglasses are those as commercialized under the name "Bioglass45S5", or those having a composition as follows: 45-55% $SiO_2$, 10-25% ($K_2O+Na_2O$), 0-5% MgO; 10-25% CaO; 0-2% $P_2O_5$ and 0-1% $B_2O_3$ in weight, to the total weight of the bioglass. A preferred bioglass has the following composition: 45% $SiO_2$, 24.5% CaO and 24.5% $Na_2O$ and 6% P2O5 in weight to the total weight of the bioglass. Another preferred bioglass has the following composition: 53% SiO2, 11% K2O and 6% Na2O 5% MgO 22% CaO and 2% P2O5 and 1% B2O3 in weight, to the total weight of the bioglass.

Lead zirconate titanate (Pb[ZrxTi1-x]O3 0<x<1), also called PZT, is a ceramic perovskite material that shows a marked piezoelectric effect.

Biocompatible polymers suitable in this invention may be methyl polymethacrylate (PMMA), polyethylene (PE), PolyEtherEtherKetone (PEEK), polyglycolic acid (PGA), polybutylic acid (PBA), polylactic acid (PLLA), polycaprolactone (PCL).

According to a first embodiment, the biomaterial of the invention is non-resorbable and uses non-resorbable materials only. According to a second embodiment, the biomaterial is fully or partly resorbable.

According to one embodiment, the biomaterials used for manufacturing the biomedical device are composite or heterogeneous material. In a preferred embodiment, the biomaterials of the invention are not composite.

According to a preferred embodiment, the biomaterial of the invention is a bioactive material i.e. a material which stimulates bone formation leading to a physico-chemical bond. According to an embodiment, the biomaterial of the second area prevents and/or discourages cell attachment and/or proliferation.

According to the invention, the absorbent is well-absorbent in the wavelengths of the energy source used during the laser sintering process. Well-absorbent means that the energy received from the energy source and dissipated from the absorbent is sufficient to bond the adjacent first powder via fusion or sintering. Advantageously, addition of the absorbent enhances the absorption of the energy source by the first powder by converting the laser energy into calorific energy.

In one embodiment, the absorbent presents, compared to the other components of the first powder, an absorption differential above 0.2, preferably above 0.4, more preferably above 0.5. The absorption coefficient (A>=0) being defined as A=1-R, where R is the reflectivity coefficient. In the wavelength from 100 nanometers to 3 micrometers, the absorption coefficient of carbon may exceed 0.7.

In one embodiment, the absorbent is in any form: liquid, solid, gas, preferably in a powder form. In one embodiment, the absorbent is in the form of a powder. In another embodiment, the absorbent is in the form of a suspension or in liquid form.

Preferably, the absorbent size ranges from 1 nanometer to 500 micrometers. More preferably, the absorbent is in the form of nanoparticles of a size ranging from 1 nanometer to 200 micrometers, preferably from 10 nanometers to 100 nanometers.

In one embodiment, the amount of absorbent is less than 5% (w/w) relative to the total weight of particles used in the process (first powder and absorbent), preferably from 0.01 to 2% (w/w), more preferably from 0.1 to 1% (w/w).

In one embodiment, the mass ratio of the absorbent to the first powder ranges from 0.000001 to 1, preferably from 0.00001 to 0.1, more preferably from 0.0001 to 0.2.

In one embodiment, the size ratio of the absorbent in the form of powder to the main first powder ranges from 0.000001 to 1, preferably from 0.00001 to 0.1, more preferably from 0.0001 to 0.1.

In one embodiment, the absorbent is inorganic, preferably a mineral. In one embodiment, the absorbent is not a polymer.

In one embodiment, the absorbent comprises carbon, scandium, titanium, vanadium, chromium, manganese, iron, cobalt, nickel, copper, or zinc or any compound comprising at least one of said chemical elements, or mixture thereof.

In one embodiment, the absorbent comprises carbon derivatives such as carbon black or carbide such as silicon carbide, calcium carbide, iron carbide, aluminum carbide, magnesium carbide, beryllium carbide, scandium carbide, yttrium carbide, lanthanum carbide, titanium carbide, zirconium carbide, hafnium carbide, vanadium carbide, niobium carbide, tantalum carbide, chromium carbide, molybdenum carbide, or mixture thereof. In one embodiment, the absorbent comprising carbon may comprise carbon free or carbon no free or mixture thereof. In one embodiment, the absorbent comprising carbon may be silicon carbide or carbon-such as for instance carbon black-; preferably with purity from 85 to 99.999%, more preferably with purity from 95 to 99.999%; or a mixture thereof. In one embodiment, the absorbent has a purity ranging from 85 to 99.999%, more preferably from 95 to 99.999%.

Advantageously, the absorbent dopes the laser sintering process, by providing a rapid manufacturing method compatible with any kind of first powder, particularly not or poorly absorbent powders such as ceramic powders. The use of absorbent is particularly useful for laser sintering ceramic powders such as calcium phosphate, particularly hydroxyapatite or tricalcium phosphate; for example pure white powder of hydroxyapatite which is totally "transparent" to Nd-YAG laser (wavelength of 1064 nanometers) but being commonly used in industrial applications.

According to one embodiment, the biomedical device manufactured by a laser sintering process comprises several areas (i.e. several zones characterized by their degree of controlled porosity), the first peripheral area being the most porous, and the several underlying areas are preferably ordered to form a gradient of porosity in relation to one another. Said several areas also have a controlled porosity decreasing with each successive area away from the first area. According to one embodiment, the first area comprises itself several areas. In one embodiment, the second area comprises itself several areas (as seen in FIG. 4).

According to one embodiment the second area has a controlled (i.e. programmed) porosity. According to another embodiment, the second area is not porous. According to one embodiment, the first and/or second area has a non-uniform porosity within the volume of said area(s). According to one embodiment, the first and/or second area has a homogeneous size pores and a homogeneous spatial pore distribution within the volume of said area(s). Homogenous means that said pores have constant programmed dimensions (size, diameter, length . . . ) and are distributed at regular programmed intervals.

According to a preferred embodiment, the three-dimensional biomedical device of the invention, having an osteoconductive first area with a controlled porosity and a second area, is such that the ratio of the porosity of the second area to the porosity of the first area being equal or less than one, preferably ranging from 0.001 to 0.9, preferably from 0.1 to 0.85, more preferably from 0.0111 to 0.83, more preferably ranging from 0.03 to 0.2 even more preferably from 0.033 and 0.166.

According to one embodiment, said first area is colonized by cells. According to one embodiment, said first area is more colonized by cells than the second area. Advantageously, material and/or porosity and/or dimensions of said first area are selected in order to promote cell colonization.

According to a particular embodiment, the three-dimensional biomedical device of the invention has an osteoconductive first area with a controlled porosity and a second area, is produced by a laser technology from a powder comprising a substantially not degradable hydroxyapatite, said powder being free of any metal or bone component, the ratio of the porosity of the second area to the porosity of the first area being equal or less than one, preferably ranging from 0.001 to 0.9 preferably from 0.1 to 0.85, more preferably from 0.0111 to 0.83, more preferably ranging from 0.03 to 0.2, even more preferably from 0.033 and 0.166.

In one embodiment, the first area has a at least one dimension, preferably the thickness, ranging from 0.01 millimeter to 5 centimeters, or from 0.01 millimeter to 3 centimeters, or from 0.01 millimeter to 4 centimeters, or from 0.01 millimeter to 2 centimeters; or from 0.01 millimeter to 1 centimeter, or from 0.01 millimeter to 50 millimeters, or from 0.01 millimeter to 25 millimeters, or from 0.01 millimeter to 10 millimeters or from 0.01 millimeter to 1 millimeter. According one other embodiment, the first area has at least one dimension, preferably the thickness, adapted for exhibiting capacity of cell migration enabling osteoconduction. Preferably, the at least one dimension corresponds to the minimum covering-thickness of the first area around or onto the underlying second area.

According one embodiment, the three-dimensional biomedical device is a core/sheath structure wherein the second area is a core region and the first area extends over at least a part of said core region. According to an embodiment, the three-dimensional biomedical device comprises a first area which extends totally over the second area. According one other embodiment, the three-dimensional biomedical device is a plate with a first layer (corresponding to the first area) and a second layer (corresponding to the second area) and the three-dimensional biomedical device is designed for being implanted into a defect wherein only the first layer is in contact with bone tissue, when in situ. According to a preferred embodiment, the second area is only in contact with the first area and/or, when in situ, with any other biological tissue than bone for example articular cartilage, muscle tissue, epithelial tissue, nervous tissue etc.

In one embodiment, the three-dimensional biomedical device is a solid body. In one embodiment, the three-dimensional biomedical device is a hollow body. In one embodiment, the three-dimensional biomedical device is not a hollow body.

According to one embodiment, said second area is not colonized by cells. According to one embodiment, said second area is less colonized by cells than the first area. Advantageously, material and/or controlled porosity and/or dimensions of said second area are selected in order to prevent or minimize cell colonization.

According to one embodiment, the porosity is controlled i.e. programmed and defined before the laser sintering process. According to a preferred embodiment, the porosity does not result from the degradation of a substrate, the injection of a gas and more generally from a chemical reaction.

According to a particular embodiment, the three-dimensional biomedical device is not produced by a unique process of depositing, ejecting or dispensing a liquid, a semi-liquid, a solid or a semi-solid. More particularly, the three-dimensional biomedical device of the invention is not totally produces by ink-jet printing. According one other embodiment, the three-dimensional biomedical device is not made by solidification using a source of energy other than laser energy for example aggregation, coagulation, cross-linking, reticulation, jellification or polymerization of a liquid, semi-liquid, solid or semi-solid solution. According to a preferred embodiment, the three-dimensional biomedical device is manufactured without any other additives or absorbent such as a chemical component; a gas; a solvent; a binder such as a light and/or heat sensitive polymeric binder; or a precursor. According to one embodiment, the three-dimensional biomedical device is not manufactured by impregnating of a substrate with a powder or a liquid.

Advantageously, the first area which is an osteoconductive porous matrix has a controlled structure, more particularly a controlled porosity which is selected, defined and programmed before manufacturing. In one embodiment, the controlled structure is defined by a controlled porosity for example pore sizes (width, length or diameter, shape), pore orientations, pore distributions and interconnections. In one other embodiment, the controlled structure is defined as a design parameter in the laser sintering process. In one embodiment, the controlled structure is defined for being a regular or a randomized pattern. The quality of the porosity (macroporosity) of the first area is preferably controlled by the virtual object obtained from an image of the defect or by the 3D image laser. In one embodiment, the data imaging which allows manufacturing the present invention is received from MRI, X-RAY, CT, Ultrasound, LASER interferometry or PET scanning. This data imaging is then used to derive a 3D solid model of the defect.

According to an embodiment, when the implant is placed in the defect, the first area, which is more porous than the second area, is contacting or close to the natural tissue bordering the defect. According an embodiment, only the first area is in contact, in situ, with natural tissue, more particularly with the limits or borders of the defects. According to a preferred embodiment, the first area is in contact, in situ, with natural bone and the second area is not in contact with the natural bone. Advantageously, the first area is at the periphery of the implant. Even more advantageously, the first area borders and surrounds the second area thus spatially isolating the second area from the natural tissue for example cancellous and compact bone or bone marrow.

According to an embodiment, the pores of the first area have a diameter 10 to 1000 micrometers, preferably from 100 to 800 micrometers, more preferably from 200 to 600 micrometers, even more preferably 300 to 500 micrometers.

According to an embodiment, the pores of the second area have a diameter from 1 to 100 micrometers, preferably from 1 to 80 micrometers, more preferably from 2 to 60 micrometers, even more preferably 5 to 50 micrometers.

Advantageously the porosity of the matrix is controlled and programmed in such a way that the first area behave as an osteoconductive support. Advantageously, the porosity in the first area may range from 20 to 90 vol %, and preferably from 30 to 80 vol %. The term "vol %" means volume percentage, corresponding to the ratio of the volume of vacuity to the full volume.

According to another embodiment, the second area is such that its porosity is comprised between 0 and 25 vol %, preferably 0 and 10% vol % more preferably of about 0 and 5 vol %. Consequently, the properties of the implant in the second area are different from the properties of the implant in the first area. According to an embodiment, the second area occupies a larger surface in the implant that the first area. According to one embodiment, the first and the second areas have different mechanical properties for example tensile or compressional strength, flexural strength, elastic and/or plastic limits toughness etc. According to one embodiment, the first and the second areas have different osseointegration properties for example the first area is more osteoconductive and/or osteoinductive than the second area.

According to an embodiment of the invention, the first area has a compression resistance ranging from 20 to 60 MPa, preferably ranging from 30 to 50 MPa, more preferably of about 40 MPa; the second area has a compression resistance of 80 to 150 MPa, preferably 90 to 120 MPa, more preferably of about 100 MPa.

According to a preferred embodiment, the second area has superior mechanical properties such as strength or rigidity than the first area i.e. the second area has a superior ability to withstand mechanical constraints applied on the implant.

Advantageously, the first area allows osseointegration, i.e. a stable anchorage of the three-dimensional biomedical implant achieved by direct bone-to-implant contact; and the second area prevents or discourages cell attachment due to a low porosity and the lack of direct contact with the tissue surrounding the first area and provides mechanical support.

According to an embodiment, the biomaterial of the invention is such that the first area and the second area are made from the same initial powder material, which preferably consists of synthetic hydroxyapatite only.

According to an embodiment, the first powder and/or the absorbent used for manufacturing the invention is a dry powder. According to one other embodiment, the biomaterial is not based on a foam, a sponge or a mesh in any step of the manufacturing process. According to an embodiment, the three-dimensional biomedical device is not made from a liquid or a semi-liquid such as a viscous solution, a paste, a slurry or a mixture of a powder and a liquid in any step of the manufacturing process. "Made from" means that the biomedical device is manufactured with a defined raw material which is a part of the biomaterial composition of the biomedical device.

In this embodiment, the biomaterial of the invention is a three-dimensional multilayered biomedical device, having at least 2-1000 layers, preferably 5-500 layers, more preferably 10-400 layers, each layer being made from one powder material.

According to an embodiment, the biomaterial may be a composite biomaterial: in an embodiment, the biomedical has 2-1000 layers, least 2-1000 layers, preferably 5-500 layers, more preferably 10-400 layers, and at least two layers being made from non-identical first powder materials.

Advantageously, the first and last layers are of one material, such as for example hydroxyapatite, and the inside layers are of a second material, such as for example a metal or metal alloy, advantageously titane or nitinol. In this embodiment, the finished implant may be such that its periphery is made of the one material, in our example hydroxyapatite, whereas its core is made of the second material, in our example metal or metal alloy.

In a preferred embodiment, the thickness of the absorbent selectively deposited onto the first powder ranges from 1 nanometer to 1 millimeter, 10 nanometers to 500 micrometers, 10 nanometers to 250 micrometers, 10 nanometers to 50 micrometers, 10 nanometers to 10 micrometers, 10 nanometers to 1 micrometer, 10 nanometers to 500 nanometers, 10 nanometers to 250 nanometers, 10 nanometers to 100 nanometers or 10 nanometers to 50 nanometers.

In one embodiment, the absorbent selectively deposited onto the first powder is a nanometric layer, preferably a layer made of 1 atom to 1000 atoms, 1 atom to 500 atoms, 1 atom to 250 atoms, 1 atom to 100 atoms or 1 atom to 50 atoms.

In a preferred embodiment, said absorbent is locally deposited on the defined areas which are processed by the laser beam during the laser sintering process.

In one embodiment, the absorbent is partially deposited on the layer of first powder.

In a preferred embodiment, said absorbent is selectively deposited by means of a nozzle, a spray, a jet or a printing head or any means for spreading particles in a solid, gaseous or liquid form known by skilled in the art.

In another embodiment, the material is made of a porous colonizable first area, which may be hydroxyapatite or tricalcium phosphate and a tight second area which may have a further function of reservoir for drug release.

In a further embodiment, the biomaterial of the invention includes a first peripheric area which may be hydroxyapatite, and a second core area, which may be TZP.

In a still further embodiment, the biomaterial of the invention includes a first area of hydroxyapatite, and a second area of ceramics such as for example zirconia, or metal or metal alloy.

In a still further embodiment, the biomaterial of the invention includes a first area of tricalcium phosphate, and a second area of ceramics such as for example zirconia, or metal or metal alloy.

The biomaterial of the invention may thus be non-uniformly porous. Non-uniform porosity allows for permeability (i.e. osteoconductivity) at some regions and not at others, within the biomaterial, or the extent of permeability may differ within the first area, if needed. According to an embodiment, the first area is gradated from a high porosity at its edge, to a lower porosity at its core.

According to another embodiment, the first and/or the second area includes spacers to make a biomaterial close to the alveolar bone, where the spacers play the role of the voids of the bone. The spacers are made of ceramics and are means for maintaining spaces, preferably a hollow space, within the biomaterial.

According to an embodiment, the biomaterial of the invention may comprise one or more pharmaceutical agents or biomolecules, or combinations thereof. The pharmaceutical agent may be any agents, although it is envisaged that the most useful agents will be those that e.g. promote healing, prevent infection, reduce inflammation, minimize or prevent pain, stimulate the influx of healing cells, or act as a immunosuppressant. The term "biomolecules" in this context includes cells, for example stem cells or progenitor cells. The biomolecules may be selected from the group consisting of: cells, cytokines, growth factors, hormones or combinations thereof.

In a particular embodiment of the invention, the first area, prior to implantation, is seeded or colonized by tissue forming cells immunologically compatible with the eventual implant recipient.

In a particular embodiment of the invention, the first area, prior to implantation, is seeded or colonized by tissue forming cells, such as for example stem cells or stem cells derived cells, which are preferably immunologically compatible with the eventual patient, more preferably autologous cells.

In a further embodiment, the first area, prior to implantation, is impregnated with a cell growth medium suitable for osteoblasts growth and/or is in contact or impregnated with growth factors. It may then seeded or colonized by tissue forming cells.

In a still further embodiment, the biomedical device of the invention is implantable.

In a preferred embodiment, the biomedical device of the invention is an implant, preferably a three-dimensional implant, more preferably a cranial implant. Preferably, this implant has a size suitable for large defects, preferably equal or larger than 25 cm², more preferably 28-100 cm². This implant may further comprise a sensor, such as for example a sensor of biological signals, preferably intracranial pressure detectors, electric micropotentials, etc.

In another embodiment, the biomedical device of the invention fits in a bone defect, optionally the biomedical device is a patient-specific implant i.e. an implant adapted to the specific anatomy of the patient and/or the shape of the defect.

In another embodiment, the biomedical device of the invention is a coating, which is coated onto an implant. In another preferred embodiment, the coating is an additional step independent of the manufacturing process of the three-dimensional device. In one other embodiment, the biomedical device of the invention is not a coating.

This invention also relates to a method for manufacturing a biomedical device of the invention, wherein:
- an image of the defect is performed through usual medical imagery means, such as for example MRI (magnetic resonance imaging), CT-scan (computerize tomography) and the image data are consolidated in a three-dimensional software such as for example "Mimics" of the MATERIALISE company in order to give a three-dimensional view;
- from this image, a virtual object is designed with a computer-aid designed software known by one skilled in the art such as for example "3-Matic" of the Materialise company or "Cathia" of the Dassault Systems company;
- optionally, a scale model (by model is meant a material subject matter), i.e. a larger or smaller object than the actual size of the virtual object designed with computer-aid software, or at the actual size of said virtual object, may be performed;
- the design of the virtual object may be reviewed and optionally corrected by the surgeon or following the instructions of the surgeon;
- upon agreement of the surgeon, the biomedical device is manufactured by a laser technology comprising layering a powder of particles, such as for example ceramic particles, more preferably substantially not degradable synthetic hydroxyapatite, onto a plate so that a layer of a predetermined thickness is formed on the plate, and having the laser beam selectively processed the powder to produce a processed layer, and this, layer after layer, the layers being joined together until the completed part is formed.

According to one embodiment, the layered powder comprises a mixture of a first powder and an absorbent in the form of a powder. In an alternative embodiment, the powder consists of first powder and the absorbent is selectively deposited thereon once the first powder has been layered. In another alternative embodiment, the first powder is coated with the absorbent.

According to one embodiment, the absorbent is coated on the first powder by wet process, chemical vapor deposition, or any process enabling coating of a powder.

According to one embodiment, the mixture of first powder and the absorbent used during the manufacturing process is obtained by wet process. In one embodiment, the solvent used during the wet process is an organic solvent, preferably methanol. In one embodiment, the mixture is prepared by mixing ⅔, by volume, of organic solvent with ⅓, by volume, of a mixture comprising the first powder and the absorbent. The previous solution is then heated to 120° C. until total evaporation.

The method of the invention is advantageous, in that it makes it possible to directly manufacture biomedical devices i.e. in a one-step manufacturing process, especially ceramic-based biomedical devices, without needing a molding step or a machining step or more generally an additive step such as for example heating step, dissolving step or using any additive components for example chemical additives, binders, gas or solvents.

The method of the invention is flexible, in that the design may perfectly be adapted to the defect and/or to the wishes of the surgeon.

According to an embodiment, the laser technology used in the process of the invention is laser powder fusion. In this embodiment, the particles of the powder are directly fused when contacted with the laser beam, thus the process of the invention avoids the use of any binding agent.

In a preferred embodiment, the machine to implement the process of the invention also comprises a heating system and/or a cooling system.

In one embodiment, the manufacturing device comprises at least one means for depositing or spreading the first powder and/or layering the first powder for example a roll or an agitator plate. In a preferred embodiment, the machine to implement the process of the invention also comprises a container for storing the absorbent.

In one embodiment, the manufacturing device further comprises a least a means for depositing an absorbent for example a nozzle, a spray, a jet, a printing head or any means for spreading particles known by skilled in the art (see FIG. 2). According to one embodiment, said at least one means for depositing an absorbent is moveable along the desired trajectory.

According to one embodiment, the manufacturing device comprises at least two deposition means. Preferably a means for layering a powder and a second means for selectively depositing an absorbent.

In one embodiment, the manufacturing device comprises at least one means for depositing or spreading the first powder and at least one means for depositing an absorbent.

In one embodiment, the manufacturing device comprises at least one energy source, for example at least one laser. In one embodiment, the laser selectively sintered or fused the powder on a pre-defined trajectory. According to one embodiment, the absorbent is selectively deposited only on said predefined trajectory prior to the sintering.

In one embodiment, the laser sintering process preferably sinters or fuses the particles together in the whole thickness of the layer and it action propagates also on the preceding layer, so that the current layer and the preceding layer actually are fused together.

In one embodiment, at the end of the laser sintering process, the not-fused residual powder is blown out by any suitable means, preferably mechanical means such as for example micro-aspiration or suction or brushing; then, the biomedical device is recovered.

In one embodiment, the first powder and the absorbent under the form of a powder are mixed before the beginning of the manufacturing process. In one embodiment, the first powder and the absorbent are mixed during the manufacturing process. In one embodiment, the first powder and the absorbent are not mixed. In said embodiment, the absorbent in the form of powder, suspension or liquid is selectively deposited onto a layer of first powder.

The process is performed from at least one powder of particles comprising ceramics; and/or metals; and/or metal alloys; and/or bioactive glasses; and/or lead zirconate titanate; and/or biocompatible polymers and/or mixtures thereof.

According to an embodiment, the particles consist of synthetic hydroxyapatite. Advantageously, for large defects this synthetic hydroxyapatite is substantially non-degradable. Preferably the hydroxyapatite powder has a purity of at least 95%.

According to another embodiment, the particles consist of tricalcium phosphate, preferably [beta]-tricalcium phosphate.

According to a further embodiment, biphasic powder the particles comprise or consist of a mixture hydroxyapatite/tricalcium phosphate in a ratio ranging from 55/45 to 90/10.

In a specific embodiment, the powder may be a mixture of particles of various natures selected in the group of alumina, hydroxyapatite, B-TCP, Zircone and titanium, titanium alloys such as for example titanium-aluminium-vanadium, chrome-cobalt and alloys thereof.

The particles may have a granulometry of 1 to 500 micrometers, preferably 5 to 100 micrometers, more preferably 10 a 25 micrometers.

The plate may be slightly rough. This embodiment makes it easier for the first layer of particles to hook up onto the plate.

According to an embodiment, the layering device is a titanium plate, possibly coated with a film of hydroxyapatite prior to the beginning of the building of the piece; the coating may be carried out by a powder projection process such as for example "D gun". This kind of coating of the plate may help having a good hook of the powder on the plate, and may help the layering of the first layer.

According to an embodiment of the process of the invention, the powder is layered with a layering device; the layering device may be a roll, such as for example a ceramic roll. According to another embodiment, the layering device is a blade, such as for example a metallic blade.

The thickness of the layer of powder may be adjusted at a predetermined value, which may for example be of 0.1 to 2000 micrometers or 0.1 to 1500 micrometers or 10 to 1000 micrometers, preferably of 50 to 500 micrometers, more preferably 70 to 100 micrometers. In one embodiment, the thickness of the layer is defined depending on the desired resolution of the three-dimensional biomedical device.

According to an embodiment, the powder may be heated prior to the layering step, at a temperature of 200 to 1500° C., preferably of 500 to 1200° C., more preferably of about 800° C. The prior heating of the powder may facilitate the processing of the powder. In a preferred embodiment, the prior step of heating is optional i.e. is not an essential step which alone may generate the three-dimensional biomedical device more particularly a controlled porosity.

According to the invention, the laser locally impacts the powder. The laser may be a pulsed laser or a continuous laser, preferably of 50 to 1200 watts, or of 100 to 1200 watts, or of 100 to 1000 watts, or of 100 to 750 watts, or of 100 to 500 watts, or of 100 to 250 watts, or of 160 watts. In an embodiment, the laser may be a solid-state laser, for example made a diode laser or laser made of crystal such as ruby or a laser YAG. In one other embodiment, the laser may be a gas-state laser, for example made of argon, helium, nitrogen, hydrogen, $CO_2$, krypton etc. In one other embodiment, the laser is a semi-conductor laser or a fiber laser. The laser power of the laser beam may be adjusted at 1 to 25% of the total power of the laser, preferably at 5%, 7% or 10% of the total power. The laser may be partially defocused (for example 10% of defocusing).

In an embodiment, the laser used generates electromagnetic radiation with a wavelength of from 100 nanometers to 1 millimeter, or 100 nanometer to 500 micrometers, or 100 nanometers to 100 micrometers, or 100 nanometers to 10 micrometers, or 100 nanometers to 2 micrometers, or 100 nanometers to 1 micrometer.

Sintering is the process of forming a solid mass of material without melting it to the point of liquefaction. The atoms in the materials diffuse across the boundaries of the particles, fusing the particles together and create one solid piece At the point of impact of the laser, the powder of particles fuses. The trajectory of the laser, which is defined by computer means to reproduced the computer-aid designed object, defines the shape of the object made from the processed particles, in the thickness of the layer, more particularly the laser design the shape of the controlled porosity layer after layer. The laser beam is modulated on and off during the raster scan so that the powder is sintered when the aim of the beam is directed according to a modelisation of the three-dimensional device. The three-dimensional biomedical device is thus manufactured in a one-step-process by laser sintering.

According to one embodiment, the use of an absorbent enables increasing the progression speed of the laser beam. The progression speed of the laser beam may range from 0.01 and 5000 mm/s; or 0.01 and 1000 mm/s; or 0.01 and 500 mm/s; or 0.01 and 250 mm/s; or 0.01 and 100 mm/s; or 0.01 and 50 mm/s, or from 0.1 and 25 mm/s; or from 0.1 and 10 mm/s, or from 1 and 4 mm/s Progression speed means the velocity of the laser focus beam across the powder bed and therefore determines the speed of manufacture. The progression of the laser beam along the layer according to a predefined trajectory creates the shape of the device by sintering particles of the layer, more particularly the specific pattern leading to a controlled porosity of each first and second area.

Advantageously, the use of the absorbent enables to enhance the amount of linear energy without increasing the power of the laser and/or lowering the speed of the movement of the laser beam or using other sources of energy in order to compensate the low absorption of the first powder. Linear energy means the amount of energy transferred by an ionizing particle (e.g. a photon laser) traversing a material medium to an adjacent material. It depends on the nature of the radiation as well as on the material traversed. When a layer is processed, a further layer is spread and laser processed. The trajectory of the laser may have a deviation between the laser beams and the deviation may range from 50 to 150 micrometers, preferably from 70 and 110 micrometers.

According to an embodiment, the plate is supported by a tray and the tray is movable up and down. In this embodiment, when a layer is processed, the tray is moved down prior to the processing of the next layer. In one embodiment, it may be possible to move the laser beam for example by means of mirrors or conducting cables; or to move plate wherein the powder is lied on.

According to another embodiment, the plate is located within a container, which is preferably tight. Preferably, the container is a furnace or an oven, so that the powder may be easily heated.

Layer after layer, with reference to the 3D designed object, the full biomedical device is made. The non-processed powder is blown out.

According to an embodiment, a further optional step of thermic post-treatment may be performed, wherein the biomedical device is reheated at a temperature of 200 to 1200° C., preferably 250 to 1000° C., more preferably around 300°-500° C. The final biomedical device is then recovered. According to one embodiment, said thermic post-treatment decreases the porosity of the second and/or first area of the three-dimensional device. According to one other embodiment, said thermic post-treatment increases the porosity of the second and/or first area of the three-dimensional device. According to one embodiment, said thermic post-treatment does not impact the porosity of the second and/or first area of the three-dimensional device. In a preferred embodiment, said post-treatment alone does not lead to the creation a controlled porosity of the three-dimensional biomedical device.

In a yet embodiment, said optional step of thermic post-treatment is configured for removing any absorbent traces. Advantageously, the three-dimensional biomedical device does not include any traces of a non-biocompatible absorbent. According to one embodiment, thermic post-treatment enables the removal of the absorbent and the enhancement of the mechanical properties. According to one embodiment, the thermic post-treatment is achieved by heating the biomedical device with a heating rate of 1° C./min up to 500° C. and then a heating rate of 5 to 10° C./min up to 1200° C. and then holding the biomedical device at 1200° C. during 3 hours.

According to an embodiment, the thermic post-treatment may be performed to enhance mechanical properties of the three-dimensional biomedical implant for example rigidity or compression resistance. According to an embodiment, the thermic post-treatment may be performed as a part of a drying process, for example in order to shorten drying period of ceramics.

Another object of the invention is the use of a biomedical device according to the invention for replacing or filling of tissue defects, e.g. bone defects or cavities in animals, including humans.

According to an embodiment, the biomedical device of the invention may be used as an implant repairing defects in bone structures resulting from surgery or trauma. In this embodiment, the biomedical device of the invention may be useful to close a defect, such an opening in a skull, to protect the tissue underneath, e.g. brain tissue.

Thus, the biomedical device of the invention is an orthobiological device, resulting in a porous scaffold. It may be used in traumatology, in reconstruction surgery, in regenerative surgery, in dental surgery, in orthodontia, in orthopaedic, in cell culture or any field of application which could benefit from permanent biocompatible but substantially not degradable implant for reconstructive purposes or for functional purposes like drug delivery or pick-up of inner signals (intracranial pressure or electric potentials for instance) or transmission of signals and/or energy from outer side of the body to inner side and vice versa. The biomedical device does not intend to create a biomimetic structure imitating the configuration of the final tissue to replace i.e. does not intend to mimic the specific structure of a tissue in order to implant the mimicking structure in contact with the native specific structure of the tissue, when in situ. In one embodiment, the three-dimensional biomedical device does not mimic the bone structure i.e. the cortical and/or the cancellous bone and therefore is not implanted such as the first area is in contact with cancellous bone and the second area is in contact with the cortical bone, when in situ.

Advantageously, only the first area having the higher porosity is in contact or proximal to the limits or borders of the defects, when in situ, and then promotes cell attachment, proliferation and vascularization. Bioactive material such as ceramic further enhances osseointegration. The second area, with superior mechanical properties, is isolated from tissue by the first area and enhances mechanical properties of the global three-dimensional biomedical device. Each first and second area are sintered deeply enough to bond it together.

A first area, preferably located at the periphery of the structure, may be a matrix-type microstructure colonizable by the patient's osteoblasts.

In one embodiment, the first and the second area are directly bonded together. In a preferred embodiment, the first and the second area are not separated by a transition zone more particularly a transition zone to avoid delamination of the first and second area. In one embodiment, the first and the second area are not mechanically connected for example by means of an appropriate adhesive such as glue; screws etc.

More specifically, the biomedical device of the invention may be used as an implant to compensate bone losses such as: cranial lesions, calveria lesions, due to traumas, tumors or malformation; maxillofacial bone losses (orbital and maxillary); dental lesions with significant loss of alveolar bone.

In a preferred embodiment, the three-dimensional biomedical device is designed for being implanted such as the first area is in contact with bone for example cortical and/or cancellous bone, when in situ. In one other embodiment, the first area is in contact, when in situ, with at least two different tissues, for example bone and articular tissue.

In a preferred embodiment, the three-dimensional biomedical device is designed for being implanted such as the second area is in contact, when in situ, with tissue except bone tissue, for example cerebral tissue, muscle tissue, nervous tissue etc.

In one embodiment, the three-dimensional biomedical device is secured into the defect using standard mechanical fixations for example bone screws, preferably bone screws are screwed into the peripheral layer. In one other embodiment, the three-dimensional biomedical device is secured into the defect using standard mechanical fixations which are removable. In one other embodiment, the three-dimensional biomedical device is not secured into the defect using standard mechanical fixations.

Also, the biomedical device of the invention may be used as an implant to compensate bones losses in orthopaedic indications such as for example traumatic lesions hard to consolidate, typically significant segmental bone losses such as tibial pseudarthroses or non-union; primary bone cancer, typically Ewing sarcoma at the proximal femur; hip replacement.

According to another embodiment, the biomedical device of the invention may be a synthetic bone, preferably a hydroxyapatite synthetic bone, on and/or in which stem cells, preferably autologous stem cells, may have been seeded and/or cultured.

According to a particular embodiment, this invention is directed to an orthopedic implant for implantation into bone cavities to support bone tissue adjacent to the cavity.

The present invention will become more fully understood from the detailed description given herein below and the accompanying drawings which are given by way of illustration only, and are not intended to limit the scope of the present patent application.

FIG. 1 is a schema of a suitable device to implement the process of the invention. The machine 6 suitable for implementing the process comprises a container 1 which transfers the first powder into a furnace 3, more precisely onto a plate 2. The machine 6 also comprises a tray 10 being designed for moving up and down at a distance corresponding to the thickness of a layer and the next layer of powder is layered. The tray may also rotate. The machine further comprises a roll 5 for spreading a programmed thickness of first powder layer (optionally mixed with an absorbent) onto the plate 2 until the desired place 7. The machine 6 further comprises a galvanometric head 9 computer directed for directing the laser beam 8 with high speed and high precision. In said embodiment, the device for implementing the present invention comprises a single means for depositing a powder (e.g. a mixture of the first powder and an absorbent in powder form).

FIG. 2 is another schema of a suitable device to implement the process of the invention comprising a galvanometric head 9 and a means for depositing an absorbent 13. A layer of first powder is layered and an absorbent is selectively deposited in a predefined trajectory onto the said first layer of first powder with the deposition means 13 located above the place 7 wherein powder is sintered. In said embodiment, the device for implementing the present invention comprises a first means for depositing the first powder 10 and a second means for depositing the absorbent 13.

FIG. 3 illustrates a cylindrical bone implant wherein the peripheral first area 11 is extending around the second core area 12. Only the first area is in contact, when in situ, with the surrounding tissue therefore isolating the core second area.

FIG. 4 shows a cross-section view of a conical three-dimensional biomedical (as FIG. 2), the peripheral porous first area 11 extends around the core region 12. The peripheral first area 11 is extending around the isolated second core area 12. First area 11 has a higher porosity than the isolated second area 12.

FIG. 5 shows a cross-section view of a conical three-dimensional biomedical with the peripheral first area 11 and the second area 12. First and second areas are made themselves by several bonded areas. Each area is delineated by its degree of porosity, preferably each area 11a, 11b, 11c, 11d has a homogeneous porosity within the volume of said areas; and each area 12a, 12b, 12c has a homogeneous porosity within the volume of said areas. The layers are ordered in such a way that porosity of the first area forms a gradient: peripheral area 11a of the first area 11 has a higher porosity than the underlying area 11b which as a higher porosity than the underlying area 11c which as a higher porosity than the underlying area 11d. The second area 12 is also ordered as a gradient of porosity such that peripheral area 12a as a higher porosity than the underlying area 12b, which as a higher porosity than the underlying area 12b which has a higher porosity than the area 12c. Then, the three-dimensional biomedical device is a laminate object made of a gradient porosity structure.

FIGS. 6-7 show a cranial implant according to the present invention. The first area 11 exhibits a controlled porosity on the periphery of the cranial implant for enhancing osteointegration.

FIG. 8 illustrates a segmental tibial bone loss.

FIGS. 9-10 show a tibial implant according to the present invention. The tibial implant perfectly fits with the segmental bone loss depicted in FIG. 8. As seen in FIG. 10, the first part 11 comprises various parts 11a, 11b, 11c with different porosities, forming a gradient of porosity, from the core to the periphery.

EXAMPLES

Figure 1:
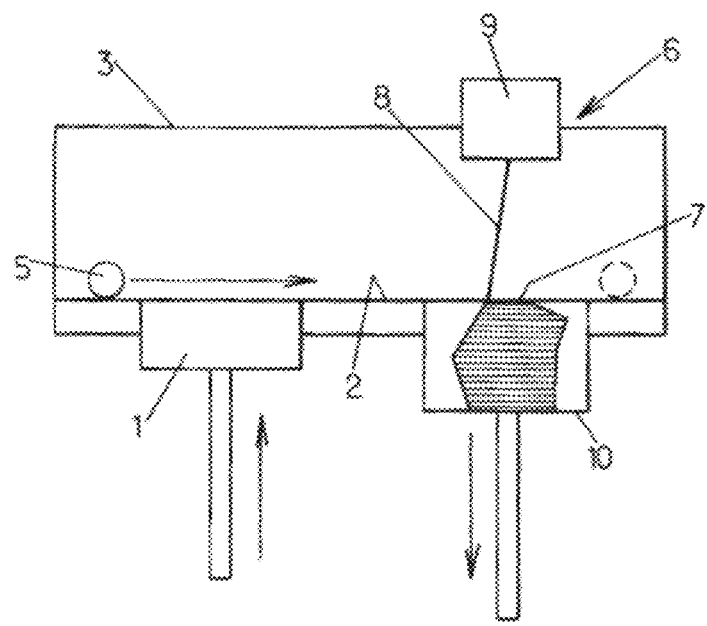
FIG. 1 is a schema of a suitable device to implement the process of the invention.
Figure 2:
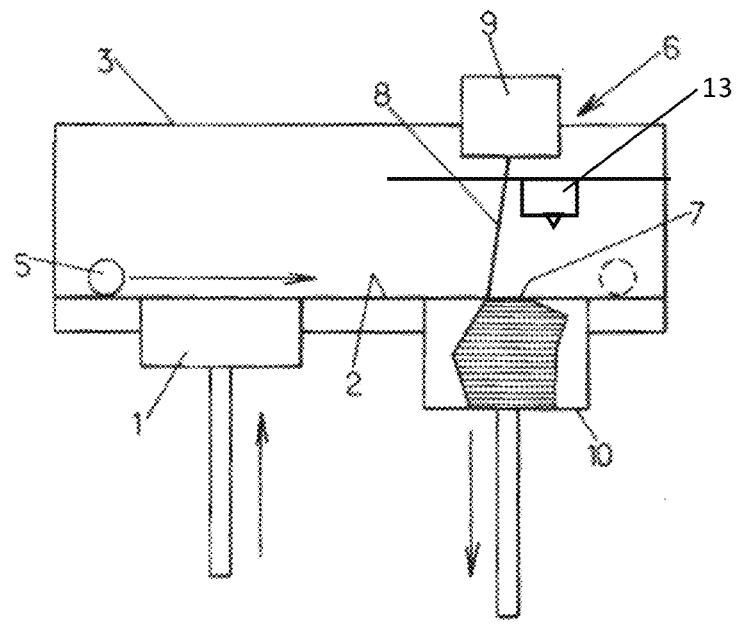
FIG. 2 is a schema of another suitable device to implement the process of the invention; said device comprising a second deposition means (e.g. for deposition of an absorbent).
Figure 3:
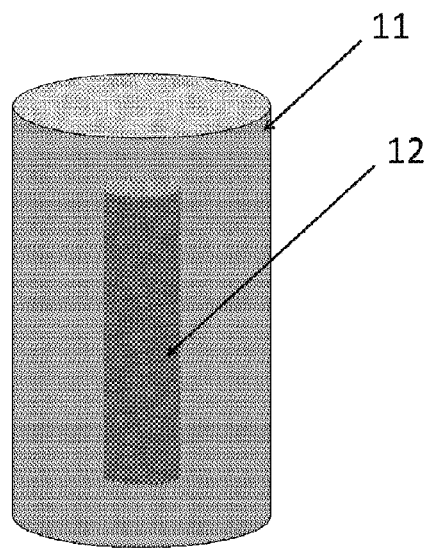
FIG. 3 is a schema showing a view of a cylindrical three-dimensional biomedical device wherein the peripheral porous first area 11 is extending around the core region 12.
Figure 4:
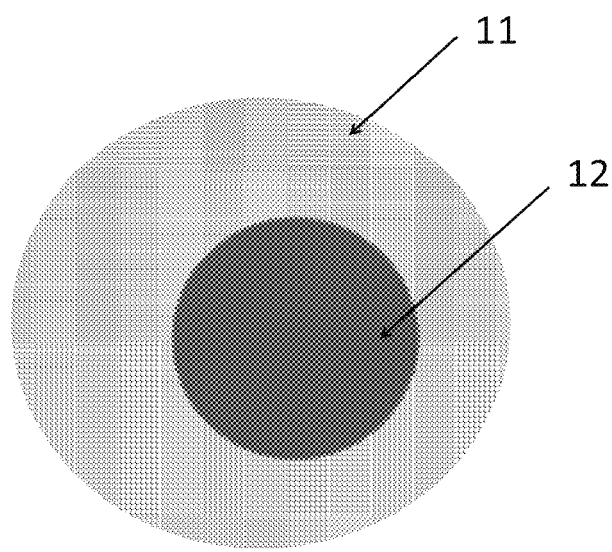
FIG. 4 is a schema showing a cross-section view of a three-dimensional biomedical device wherein the peripheral porous first area 11 is extending around the core region 12.
Figure 5:
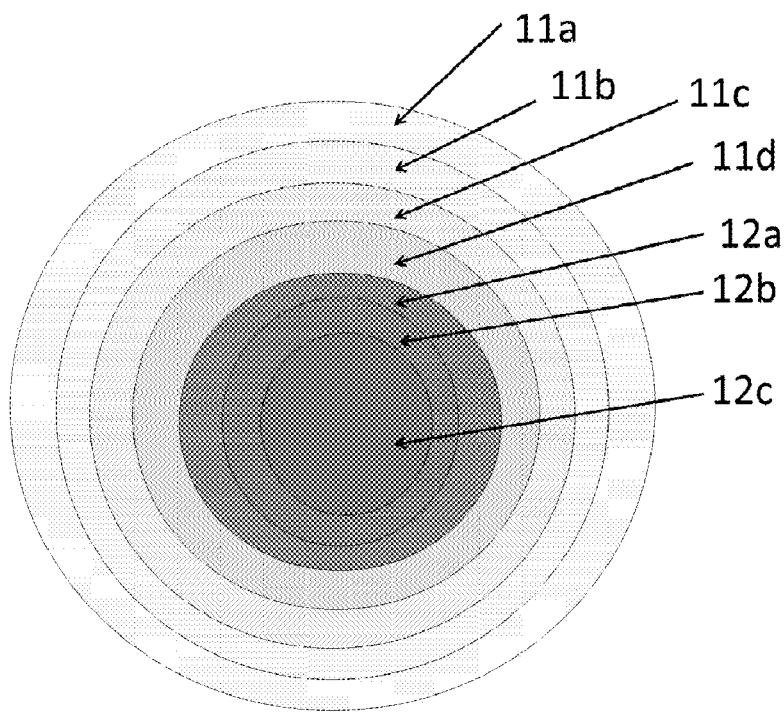
FIG. 5 is a schema showing a cross-section view of a three-dimensional biomedical device wherein the peripheral porous first area is made of several areas 11a, 11b, 11c, 11d and the second area is made of several areas 12a, 12b, and 12c.
Figure 6:
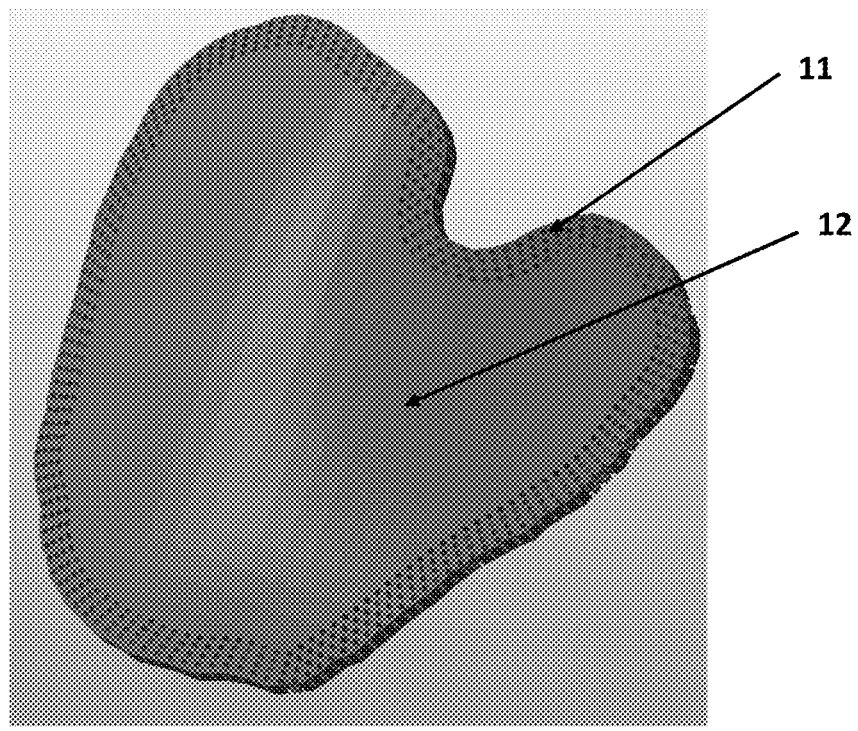
FIG. 6 represents a perspective view of a three dimensional cranial implant according to the present invention.
Figure 7:
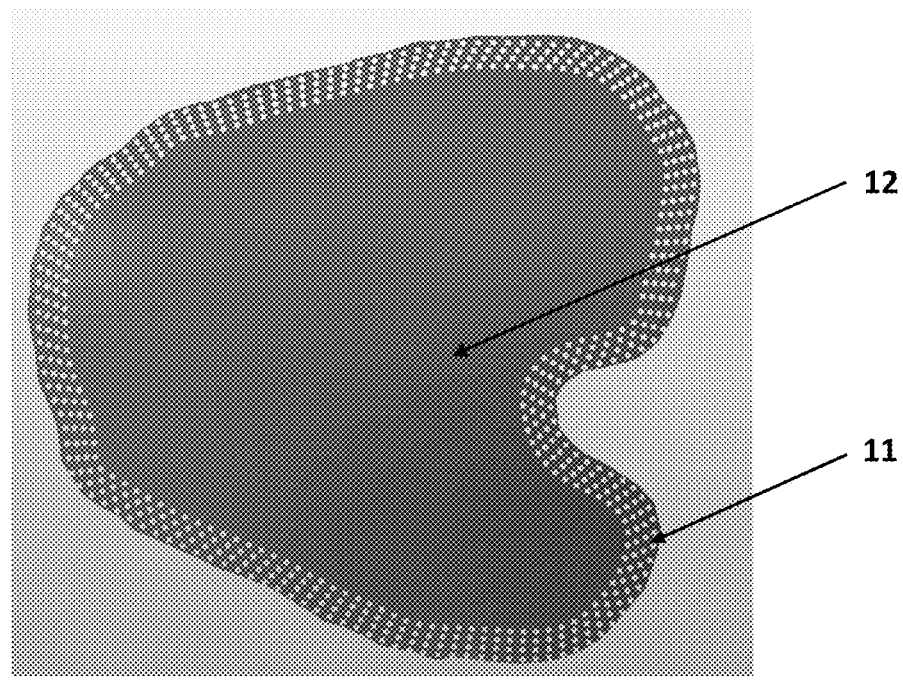
FIG. 7 represents a top view of a three dimensional cranial implant according to the present invention.
Figure 8:
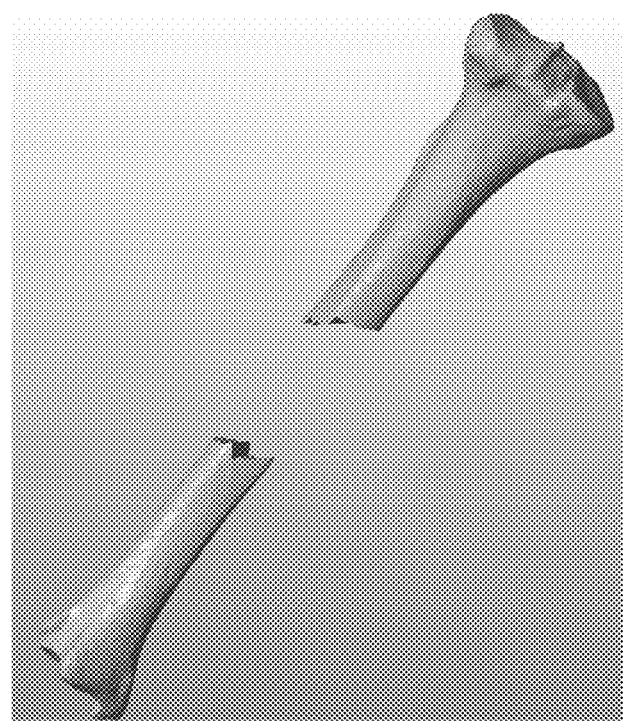
FIG. 8 represents a perspective view of segmental tibial bone loss.
Figure 9:
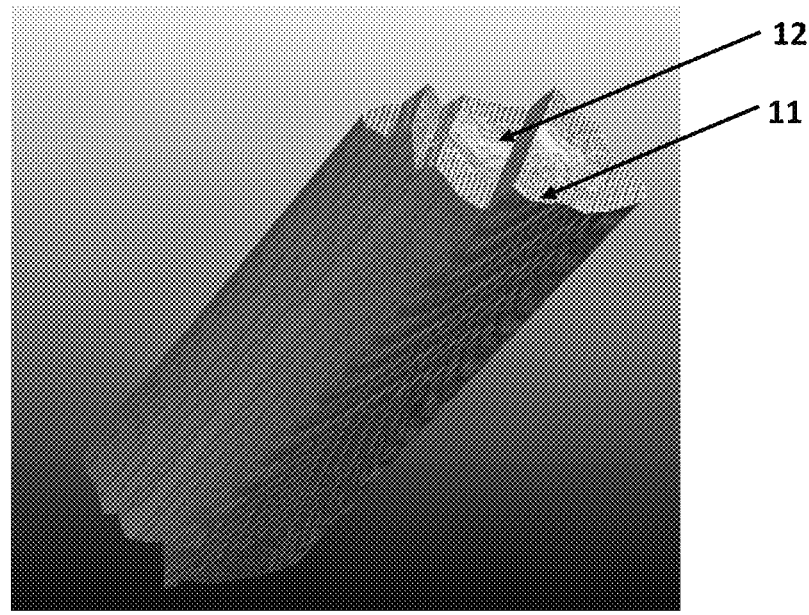
FIG. 9 represents a perspective view of a three dimensional tibial implant according to the present invention.
Figure 10:
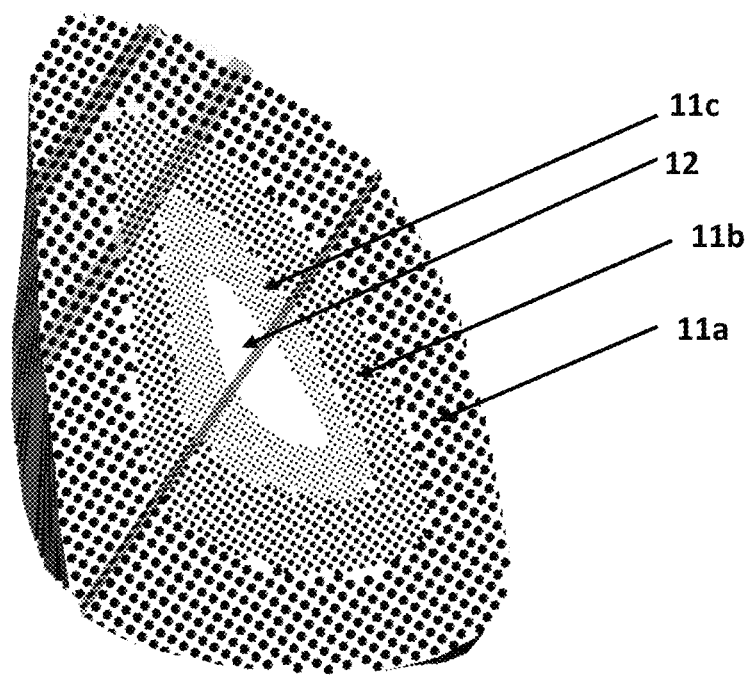
FIG. 10 represents a cross-section of the tibial implant according to the present invention.

The present invention is further illustrated by the following examples.

Example 1

The machine used may be a Phenix® PM100 device commercialized by Phenix Systems®.

A ceramic powder of hydroxyapatite having a granulometry 10 to 25 micrometers (commercial reference Medicoat®/Medipure® 20-15, purity>95%) is placed in a container 1 so that it can be layered on a plate 2. The tray 2 may be located in the furnace 3 of the machine 6. The powder may be heated to 800° C. The plate 2 may be supported by a tray 10 movable up and down. The powder is layered with a ceramic roll 5 at a place 7, where it will be processed by a laser beam 8 releases from a galvanometric head 9 (computer directed optical susceptible to direct a laser beam with high speed and high precision). The thickness of the resulting layer is of about 100 micrometers. A laser YAG 160 Watts is preferably used to locally impact and process the powder. The power of the laser beam may preferably be adjusted to 10% of the total power of the laser in order to avoid vitrification of the ceramic powder; the laser beam may be 10% defocused; the laser deviation may be 80 micrometers; the progression speed of the laser beam may be of 4 mm/s. The trajectory of the laser is defined by the 3D-image.

The data of the image (CT scan or IRM for example) are exported in a suitable format, for example DICOM. This file is imported in a software which carries out a partition of the various levels of grey and, starting from various cut-offs, rebuilds the three-dimensional anatomy of the defect. From this 3D file and a computer mediated design software, it is possible to conceive the macrostructure of the implant that fits the defect.

A first area, preferably located at the periphery of the structure, may be a matrix-type microstructure colonizable by the patient's osteoblasts.

The design of the implant is exported in a suitable format (for example format STL, IGES, DXF, HPP, OBJ) to the rapid prototyping machine, and is cut-off in slices corresponding to the thickness of the layers (for example, format SLC). The information for each layer defines the trajectory of the laser.

The trajectory of the laser designs the shape of the 3D-image in the powder, actually in the thickness of the powder. When a layer is processed, the tray supporting the plate is moved down at a distance corresponding to the thickness of a layer and the next layer of powder is layered. The process is repeated until the full biomedical device is produced.

The laser beams processes, preferably fuses the ceramic particles together in the whole thickness of the layer, and it action propagates also on the preceding layer, so that the current layer and the preceding layer actually are fused together.

At the end of the process, the not-fused residual powder is blown out by any suitable means, preferably mechanical means such as for example micro-aspiration or suction or brushing; then, the biomedical device is recovered.

Example 2

The example 1 is performed with a mixture of a first powder of hydroxyapatite and an absorbent. A powder of hydroxyapatite, having a granulometry from 5 to 25 nm and a purity above 95% (commercialized by Science Applications Industries) and an absorbent comprising carbon, having a granulometry of 40 nanometers and purity above 97%, are mixed through a wet-process; from 0.1 to 5% by weight of carbon are added to the hydroxyapatite. The mixing is conducted with a laboratory rotary evaporator, called "rotovap", using methanol as a solvent and alumina balls to promote the mixing. The ratio between the powder and the solvent is (⅓)/(⅔). The settings are the following: temperature of 120° C., speed of 25 rpm (revolution per minute) and duration of 24 hours. The rotary evaporator removes the methanol from the pulverulent substrate by evaporation. By this process, the carbon is well dispersed in the hydroxyapatite powder. The powder is then screened with a mesh size of 50 nm to remove larger particles.

The mixture of the first powder and the absorbent is then placed in a container of the PHENIX® PM100 device. Due to the addition of an absorbent, during the manufacturing process of the biomedical device, the progression speed of the laser beam is adjusted to 50 mm/s/. A biomedical device for fitting bone defect having an osteoconductive first area with a controlled porosity and a porous second area is obtained.

Example 3

The example 2 is performed with a progression speed of the laser beam of 100 mm/s. A biomedical device for fitting bone defect having an osteoconductive first area with a controlled porosity and a porous second area is obtained.

The invention claimed is:

1. A method for manufacturing a biomedical device for fitting bone defect, said biomedical device having at least one osteoconductive first area with a controlled porosity and at least one porous second area, the ratio of the porosity of the second area to the porosity of the first area being equal or less than one, wherein the device is produced by a laser technology from an absorbent and from a first powder comprising a material selected from the group consisting of ceramics, bioactive glasses, and mixtures thereof, wherein the laser is a pulsed laser or a continuous laser of 100 to 1200 watts, and the laser progression speed of the laser beam ranges from 0.01 and 5000 mm/s; and wherein
an image of the defect is performed,
from this image, a virtual object is designed with a computer-aid designed software,
optionally, a scale model is performed,
the biomedical device is manufactured by a laser technology comprising:
layering onto a plate either:
a mixture of the first powder and the absorbent;
a first powder coated with the absorbent; or
the first powder, whereon subsequently the absorbent is selectively deposited in a predefined trajectory;
so that a layer of a predetermined thickness is formed on the plate,
having the laser beam selectively processed the layer to produce a processed layer, and this, layer after layer, the layers being joined together until the completed biomedical device is formed,
wherein the ceramics are selected from the group consisting of alumina or alumina derivative, ceramic phosphates, apatite derivatives, zirconia, zirconia derivatives, zirconia-toughened alumina (ZTA), alumina-toughened-zirconia (ATZ), alumina-zircona, ytria-Zirconia (TZP), and wallostonite; and
the bioactive glasses are silicate derivatives comprising $SiO_2$, $CaO$ and optionally $Na_2O$, and/or optionally $P_2O_5$.

2. The method according to claim 1, wherein the absorbent comprises carbon, scandium, titanium, vanadium, chromium, manganese, iron, cobalt, nickel, copper, or zinc or any compound comprising at least one of said chemical elements, or mixture thereof.

3. The method according to claim 1, wherein said biomedical device comprises a mixture hydroxyapatite/tricalcium phosphate in a ratio ranging from 55/45 to 90/10.

4. The method according to claim 1, wherein the absorbent is selectively deposited by means of a nozzle, a spray, a jet or a printing head.

5. The method according to claim 1, wherein the absorbent is coated on the first powder by wet process, Chemical Vapor Deposition.

6. The method according to claim 1, wherein the particles of the first powder have a granulometry of 1 to 500 micrometers.

7. The method according to claim 1, wherein the particle size of the absorbent ranges from 1 nanometer to 500 micrometers.

8. The method according to claim 1, wherein the thickness of the layer of powder ranges from 0.1 to 2000 micrometers.

9. The method according to claim 1, further comprising a step of heating the powder prior to the layering step, at a temperature of 200 to 1500° C.

10. The method according to claim 1, further comprising a step of thermic post-treatment at a temperature of 200 to 1200° C. for removing the absorbent.

11. The method according to claim 1, wherein the laser is a 160 watts laser.

12. The method according to claim 1, wherein the laser is adjusted at 1 to 25% of the total power of the laser.

13. The method according to claim 1, wherein the particle size of the absorbent ranges from 1 nanometer to 200 micrometers.

14. The method according to claim 1, wherein the particle size of the absorbent ranges from 10 nanometers to 100 nanometers.

\* \* \* \* \*